(12) United States Patent
Milliman

(10) Patent No.: US 8,833,630 B2
(45) Date of Patent: *Sep. 16, 2014

(54) SURGICAL INSTRUMENT WITH SAFETY MECHANISM

(71) Applicant: Covidien LP, Mansfield, MA (US)

(72) Inventor: Keith Milliman, Bethel, CT (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/180,654

(22) Filed: Feb. 14, 2014

(65) Prior Publication Data

US 2014/0158745 A1    Jun. 12, 2014

Related U.S. Application Data

(63) Continuation of application No. 13/407,972, filed on Feb. 29, 2012, now Pat. No. 8,684,248, which is a continuation of application No. 12/781,622, filed on May 17, 2010, now Pat. No. 8,146,790.

(60) Provisional application No. 61/224,855, filed on Jul. 11, 2009.

(51) Int. Cl.
*A61B 17/068* (2006.01)
*A61B 17/115* (2006.01)

(52) U.S. Cl.
CPC ........... *A61B 17/115* (2013.01); *A61B 17/1155* (2013.01)
USPC ................. 227/175.2; 227/19; 227/179.1

(58) Field of Classification Search
USPC ............... 227/19, 175.1, 176.1, 175.2, 180.1, 227/175.3, 179.1; 606/139, 219
See application file for complete search history.

(56) References Cited

U.S. PATENT DOCUMENTS

| | | | |
|---|---|---|---|
| 3,193,165 A | 7/1965 | Akhalaya et al. |
| 3,388,847 A | 6/1968 | Kasulin et al. |
| 3,552,626 A | 1/1971 | Astafiev |
| 3,638,652 A | 2/1972 | Kelley |
| 3,771,526 A | 11/1973 | Rudie |

(Continued)

FOREIGN PATENT DOCUMENTS

| | | |
|---|---|---|
| CA | 908529 | 8/1972 |
| DE | 1057729 | 5/1959 |

(Continued)

OTHER PUBLICATIONS

European Examination Report dated May 13, 2014 issued in European Application No. 10 251 240.7.

*Primary Examiner* — Scott A. Smith

(57) ABSTRACT

A surgical instrument including a handle assembly, a safety mechanism, an elongated body portion and a head portion is disclosed. The handle assembly includes a stationary handle, an approximation mechanism, and a firing trigger. A lever of the safety mechanism is movable between a first position where the firing trigger is prevented from being actuated, and a second position where the firing trigger is able to be actuated. A first jaw member of the head portion is movable in relation to a second jaw member of the head portion between spaced and approximated positions. Movement of the first jaw member in relation to the second jaw member from the approximated position towards the spaced position causes the lever of the safety mechanism to move from its second position to its first position.

13 Claims, 10 Drawing Sheets

(56) References Cited

U.S. PATENT DOCUMENTS

| | | |
|---|---|---|
| 4,198,982 A | 4/1980 | Fortner et al. |
| 4,207,898 A | 6/1980 | Becht |
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,527,724 A * | 7/1985 | Chow et al. ........................ 227/8 |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,681,108 A | 7/1987 | Rosati et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,622 A | 1/1990 | Green et al. |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,240,163 A * | 8/1993 | Stein et al. ................. 227/175.3 |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balázs et al. |
| 6,264,086 B1 | 7/2001 | McGuckin, Jr. |
| 6,269,997 B1 | 8/2001 | Balázs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |

(56) References Cited

U.S. PATENT DOCUMENTS

| | | |
|---|---|---|
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 7,032,798 B2 | 4/2006 | Whitman et al. |
| 7,059,331 B2 | 6/2006 | Adams et al. |
| 7,059,510 B2 | 6/2006 | Orban, III |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,303,106 B2 * | 12/2007 | Milliman et al. .......... 227/175.1 |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 * | 4/2008 | Milliman ................... 227/175.1 |
| 7,398,908 B2 | 7/2008 | Holsten et al. |
| 7,399,305 B2 | 7/2008 | Csiky et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,717,313 B2 | 5/2010 | Criscuolo et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,784,663 B2 | 8/2010 | Shelton, IV |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,080 B2 | 11/2010 | Schwemberger |
| 7,845,536 B2 | 12/2010 | Viola et al. |
| 7,857,187 B2 | 12/2010 | Milliman |
| 7,866,527 B2 | 1/2011 | Hall et al. |
| 7,886,951 B2 | 2/2011 | Hessler |
| 7,909,039 B2 | 3/2011 | Hur |
| 7,918,377 B2 | 4/2011 | Measamer et al. |
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |
| 7,951,166 B2 | 5/2011 | Orban, III et al. |
| 7,959,050 B2 | 6/2011 | Smith et al. |
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,554 B2 | 9/2011 | Milliman |
| 8,016,858 B2 | 9/2011 | Whitman |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,113,405 B2 * | 2/2012 | Milliman ................... 227/175.1 |
| 8,146,790 B2 * | 4/2012 | Milliman ................... 227/175.2 |
| 8,348,122 B2 * | 1/2013 | Milliman et al. .......... 227/175.1 |

(56) References Cited

U.S. PATENT DOCUMENTS

| | | |
|---|---|---|
| 8,684,248 B2 | 4/2014 | Milliman |
| 2001/0000903 A1 | 5/2001 | Heck et al. |
| 2001/0010320 A1 | 8/2001 | Bolduc et al. |
| 2001/0054636 A1 | 12/2001 | Nicolo |
| 2002/0020732 A1 | 2/2002 | Adams et al. |
| 2002/0047036 A1 | 4/2002 | Sullivan et al. |
| 2002/0063143 A1 | 5/2002 | Adams et al. |
| 2002/0185516 A1 | 12/2002 | Heck et al. |
| 2002/0185517 A1 | 12/2002 | Vresh et al. |
| 2003/0019905 A1 | 1/2003 | Adams et al. |
| 2003/0047582 A1 | 3/2003 | Sonnenschein et al. |
| 2003/0057251 A1 | 3/2003 | Hartwick |
| 2003/0065342 A1 | 4/2003 | Nobis et al. |
| 2003/0073981 A1 | 4/2003 | Whitman et al. |
| 2003/0089757 A1 | 5/2003 | Whitman |
| 2003/0111507 A1 | 6/2003 | Nunez |
| 2003/0127491 A1 | 7/2003 | Adams et al. |
| 2003/0132267 A1 | 7/2003 | Adams et al. |
| 2003/0144675 A1 | 7/2003 | Nicolo |
| 2003/0178465 A1 | 9/2003 | Bilotti et al. |
| 2003/0183671 A1 | 10/2003 | Mooradian et al. |
| 2003/0192936 A1 | 10/2003 | Hartwick |
| 2003/0192937 A1 | 10/2003 | Sullivan et al. |
| 2003/0201301 A1 | 10/2003 | Bolduc et al. |
| 2003/0218047 A1 | 11/2003 | Sharma et al. |
| 2003/0222117 A1 | 12/2003 | Orban, III |
| 2004/0092960 A1 | 5/2004 | Abrams et al. |
| 2004/0092974 A1 | 5/2004 | Gannoe et al. |
| 2004/0118896 A1 | 6/2004 | Sharma et al. |
| 2004/0134964 A1 | 7/2004 | Adams et al. |
| 2004/0153124 A1 | 8/2004 | Whitman |
| 2004/0232198 A1 | 11/2004 | Adams et al. |
| 2005/0051597 A1 | 3/2005 | Tolendano |
| 2005/0067454 A1 | 3/2005 | Vresh et al. |
| 2005/0087580 A1 | 4/2005 | Orban, III |
| 2005/0107813 A1 | 5/2005 | Gilete Garcia |
| 2005/0116009 A1 | 6/2005 | Milliman |
| 2005/0125009 A1 | 6/2005 | Perry et al. |
| 2005/0143758 A1 | 6/2005 | Abbott et al. |
| 2005/0145674 A1 | 7/2005 | Sonnenschein et al. |
| 2005/0145675 A1 | 7/2005 | Hartwick et al. |
| 2006/0000869 A1 | 1/2006 | Fontayne |
| 2006/0011698 A1 | 1/2006 | Okada et al. |
| 2006/0047307 A1 | 3/2006 | Ortiz et al. |
| 2006/0047308 A1 | 3/2006 | Ortiz et al. |
| 2006/0085032 A1 | 4/2006 | Viola |
| 2006/0085033 A1 | 4/2006 | Criscuolo et al. |
| 2006/0085034 A1 | 4/2006 | Bettuchi |
| 2006/0085035 A1 | 4/2006 | Viola |
| 2006/0097025 A1 | 5/2006 | Milliman et al. |
| 2006/0108393 A1 | 5/2006 | Heinrich et al. |
| 2006/0144897 A1 | 7/2006 | Jankowski et al. |
| 2006/0151567 A1 | 7/2006 | Roy |
| 2006/0191975 A1 | 8/2006 | Adams et al. |
| 2006/0201989 A1 | 9/2006 | Ojeda |
| 2006/0201993 A1 | 9/2006 | Hur |
| 2006/0241692 A1 | 10/2006 | McGuckin, Jr. et al. |
| 2006/0255090 A1 | 11/2006 | Milliman et al. |
| 2006/0289601 A1 | 12/2006 | Orban, III |
| 2007/0023475 A1 | 2/2007 | Csiky |
| 2007/0027473 A1 | 2/2007 | Vresh et al. |
| 2007/0029363 A1 | 2/2007 | Popov |
| 2007/0034666 A1 | 2/2007 | Holsten et al. |
| 2007/0034667 A1 | 2/2007 | Holsten et al. |
| 2007/0034668 A1 | 2/2007 | Holsten et al. |
| 2007/0038248 A1 | 2/2007 | Heinrch |
| 2007/0060952 A1 | 3/2007 | Roby et al. |
| 2008/0142566 A1 | 6/2008 | Gresham et al. |
| 2009/0212088 A1 | 8/2009 | Okada et al. |
| 2009/0230170 A1 | 9/2009 | Milliman |
| 2009/0236388 A1 | 9/2009 | Cole et al. |
| 2009/0236389 A1 | 9/2009 | Cole et al. |
| 2009/0236390 A1 | 9/2009 | Cole et al. |
| 2009/0236391 A1 | 9/2009 | Cole et al. |
| 2009/0236392 A1 | 9/2009 | Cole et al. |
| 2009/0236394 A1 | 9/2009 | Cole et al. |
| 2009/0236396 A1 | 9/2009 | Cole et al. |
| 2009/0236397 A1 | 9/2009 | Cole et al. |
| 2009/0236398 A1 | 9/2009 | Cole et al. |
| 2009/0236400 A1 | 9/2009 | Cole et al. |
| 2009/0236401 A1 | 9/2009 | Cole et al. |
| 2009/0242612 A1 | 10/2009 | Adams et al. |
| 2009/0250502 A1 | 10/2009 | Milliman |
| 2009/0255976 A1 | 10/2009 | Marczyk et al. |
| 2009/0302089 A1 | 12/2009 | Harari et al. |
| 2009/0321496 A1 | 12/2009 | Holsten et al. |
| 2010/0001036 A1 | 1/2010 | Marczyk et al. |
| 2010/0001037 A1 | 1/2010 | Racenet et al. |
| 2010/0019016 A1 | 1/2010 | Edoga et al. |
| 2010/0025452 A1 | 2/2010 | Whitman |
| 2010/0038401 A1 | 2/2010 | Milliman et al. |
| 2010/0051668 A1 | 3/2010 | Milliman et al. |
| 2010/0059571 A1 | 3/2010 | Chen et al. |
| 2010/0065607 A1 | 3/2010 | Orban, III et al. |
| 2010/0065609 A1 | 3/2010 | Schwemberger |
| 2010/0084453 A1 | 4/2010 | Hu |
| 2010/0089971 A1 | 4/2010 | Milliman et al. |
| 2010/0096435 A1 | 4/2010 | Fuchs et al. |
| 2010/0108739 A1 | 5/2010 | Holsten et al. |
| 2010/0108740 A1 | 5/2010 | Pastorelli et al. |
| 2010/0108741 A1 | 5/2010 | Hessler et al. |
| 2010/0127039 A1 | 5/2010 | Hessler |
| 2010/0133319 A1 | 6/2010 | Milliman et al. |
| 2010/0147923 A1 | 6/2010 | D'Agostino et al. |
| 2010/0155452 A1 | 6/2010 | Csiky |
| 2010/0155454 A1 | 6/2010 | Viola |
| 2010/0163598 A1 | 7/2010 | Belzer |
| 2010/0170932 A1 | 7/2010 | Wenchell et al. |
| 2010/0224668 A1 | 9/2010 | Fontayne et al. |
| 2010/0230465 A1 | 9/2010 | Smith et al. |
| 2010/0230466 A1 | 9/2010 | Criscuolo et al. |
| 2010/0230467 A1 | 9/2010 | Criscuolo et al. |
| 2010/0237132 A1 | 9/2010 | Measamer et al. |
| 2010/0258611 A1 | 10/2010 | Smith et al. |
| 2010/0264195 A1 | 10/2010 | Bettuchi |
| 2010/0270356 A1 | 10/2010 | Holsten et al. |
| 2010/0276471 A1 | 11/2010 | Whitman |
| 2010/0282813 A1 | 11/2010 | Milliman |
| 2010/0282815 A1 | 11/2010 | Bettuchi et al. |
| 2010/0301098 A1 | 12/2010 | Kostrzewski |
| 2010/0327041 A1 | 12/2010 | Milliman et al. |
| 2011/0006100 A1 | 1/2011 | Milliam |
| 2011/0006102 A1 | 1/2011 | Kostrzewski |
| 2011/0011916 A1 | 1/2011 | Levine |
| 2011/0017800 A1 | 1/2011 | Viola |
| 2011/0024476 A1 | 2/2011 | Bettuchi et al. |
| 2011/0024481 A1 | 2/2011 | Bettuchi et al. |
| 2011/0036889 A1 | 2/2011 | Heinrich et al. |
| 2011/0036894 A1 | 2/2011 | Bettuchi |
| 2011/0042440 A1 | 2/2011 | Holsten et al. |
| 2011/0042442 A1 | 2/2011 | Viola et al. |
| 2011/0042443 A1 | 2/2011 | Milliman et al. |
| 2011/0057016 A1 | 3/2011 | Bettuchi |
| 2011/0089219 A1 | 4/2011 | Hessler |
| 2011/0095067 A1 | 4/2011 | Ohdaira |
| 2011/0095068 A1 | 4/2011 | Patel |
| 2011/0095069 A1 | 4/2011 | Patel et al. |
| 2011/0095070 A1 | 4/2011 | Patel et al. |
| 2011/0101065 A1 | 5/2011 | Milliman |
| 2011/0101070 A1 | 5/2011 | Bettuchi et al. |
| 2011/0108604 A1 | 5/2011 | Adams et al. |
| 2011/0114697 A1 | 5/2011 | Baxter, III et al. |
| 2011/0114698 A1 | 5/2011 | Baxter, III et al. |
| 2011/0114699 A1 | 5/2011 | Baxter, III et al. |
| 2011/0114700 A1 | 5/2011 | Baxter, III et al. |
| 2011/0114701 A1 | 5/2011 | Hessler |
| 2011/0118761 A1 | 5/2011 | Baxter, III et al. |
| 2011/0130788 A1 | 6/2011 | Orban, III et al. |
| 2011/0139852 A1 | 6/2011 | Zingman |
| 2011/0139853 A1 | 6/2011 | Viola |
| 2011/0144640 A1 | 6/2011 | Heinrich et al. |
| 2011/0147432 A1 | 6/2011 | Heinrich et al. |
| 2011/0147434 A1 | 6/2011 | Hueil et al. |
| 2011/0147435 A1 | 6/2011 | Heinrich et al. |

(56) References Cited

U.S. PATENT DOCUMENTS

| | | |
|---|---|---|
| 2011/0192882 A1 | 8/2011 | Hess et al. |
| 2011/0210156 A1 | 9/2011 | Smith et al. |
| 2011/0220703 A1 | 9/2011 | Orban, III |
| 2011/0248067 A1 | 10/2011 | Takei |

FOREIGN PATENT DOCUMENTS

| | | |
|---|---|---|
| DE | 3301713 | 11/1989 |
| EP | 0152382 | 8/1985 |
| EP | 0173451 | 3/1986 |
| EP | 0190022 | 8/1986 |
| EP | 282157 | 9/1988 |
| EP | 0503689 | 9/1992 |
| EP | 0539762 | 5/1993 |
| EP | 1354560 A3 | 4/2004 |
| EP | 2 160 984 | 3/2010 |
| EP | 2160984 | 3/2010 |
| FR | 1461464 | 12/1966 |
| FR | 1588250 | 4/1970 |
| FR | 2443239 | 12/1979 |
| GB | 1185292 | 3/1970 |
| GB | 2016991 | 10/1979 |
| GB | 2070499 | 9/1981 |
| GB | 2141066 | 12/1984 |
| NL | 7711347 | 10/1977 |
| WO | WO 8706448 | 11/1987 |
| WO | WO 8900406 | 1/1989 |
| WO | WO 9006085 | 6/1990 |
| WO | WO-2004/032766 | 4/2004 |

\* cited by examiner

SURGICAL INSTRUMENT WITH SAFETY MECHANISM

CROSS-REFERENCE TO RELATED APPLICATIONS

This application is a continuation of U.S. patent application Ser. No. 13/407,972 filed Feb. 29, 2012, now U.S. Pat. No. 8,684,248, which is a continuation of U.S. patent application Ser. No. 12/781,622 filed May 17, 2010, now U.S. Pat. No. 8,146,790, which claims benefit of U.S. Provisional Application No. 61/224,855 filed Jul. 11, 2009, and the disclosures of each of the above-identified applications are hereby incorporated by reference in their entirety.

BACKGROUND

1. Technical Field

The present disclosure relates generally to a surgical instrument for applying surgical staples to body tissue. More particularly, the present disclosure relates to a surgical stapling instrument suitable for performing circular anastomosis and/or treatment to internal walls of hollow tissue organs.

2. Background of Related Art

Anastomosis is the surgical joining of separate hollow organ sections. Typically, an anastomosis procedure follows surgery in which a diseased or defective section of hollow tissue is removed and the remaining end sections are to be joined. Depending on the desired anastomosis procedure, the end sections may be joined by either circular, end-to-end, end-to-side, or side-to-side organ reconstruction methods.

In a circular anastomosis procedure, the two ends of the organ sections are joined by means of a stapling instrument which drives a circular array of staples through the end section of each organ section and simultaneously cores any tissue interior of the driven circular array of staples to free the tubular passage. Examples of instruments for performing circular anastomosis of hollow organs are described in U.S. Pat. Nos. 7,303,106, 6,053,390, 5,588,579, 5,119,983, 5,005,749, 4,646,745, 4,576,167, and 4,473,077, each of which is incorporated herein in its entirety by reference. Typically, these instruments include an elongated shaft having a handle portion at a proximal end to actuate the instrument and a staple holding component disposed at a distal end. An anvil assembly including an anvil rod with attached anvil head is mounted to the distal end of the instrument adjacent the staple holding component. Opposed end portions of tissue of the hollow organ(s) to be stapled are clamped between the anvil head and the staple holding component. Typically, a first actuation mechanism is used to approximate the anvil head and the staple holding component to clamp the tissue. The clamped tissue is stapled by driving one or more staples from the staple holding component so that the ends of the staples pass through the tissue and are deformed by the anvil head. Typically, a second actuation mechanism is used to fire the staples. It is also common for an annular knife to be concurrently advanced to core tissue within the hollow organ to free a tubular passage within the organ.

Besides anastomosis of hollow organs, surgical stapling instruments for performing circular anastomosis have been used to treat internal hemorrhoids in the rectum. Typically, during use of a circular stapling instrument for hemorrhoid treatment, the anvil head and the staple holding component of the surgical stapling instrument are inserted through the anus and into the rectum with the anvil head and the staple holding component in an open or unapproximated position. Thereafter, a pursestring suture is used to pull the internal hemorrhoidal tissue towards the anvil rod. Next, the anvil head and the staple holding component are approximated to clamp the hemorrhoid tissue between the anvil head and the staple holding component. The stapling instrument is fired to remove the hemorrhoidal tissue and staple the cut tissue. In other uses for hemorrhoid surgery, the stapling instrument is used to remove tissue just above the hemorrhoids in order to pull the hemorrhoids back up inside the rectum and reduce the symptoms. The staples interrupt the blood flow of the superior hemorrhoidal arterial branches, cutting off the blood supply to the tissue, thus causing the hemorrhoids to shrink.

Some surgical stapling instruments include a safety device that prevents staples from being fired before approximation of the anvil head and the staple holding component.

SUMMARY

The present disclosure relates to a surgical instrument comprising a handle assembly, a safety mechanism, an elongated body portion and a head portion. The handle assembly includes a stationary handle, an approximation mechanism, and a firing trigger. A lever of the safety mechanism is movable between a first position where the firing trigger is prevented from being actuated, and a second position where the firing trigger is able to be actuated. An approximation mechanism moves the first jaw member in relation to the second jaw member from a spaced position to an approximated position, wherein movement of the first jaw member in relation to the second jaw member from the approximated position towards the spaced position causes the lever to move from its second position to its first position.

In an embodiment, the lever is biased towards its first position. In a preferred embodiment, the safety mechanism includes a latch disposed on the lever and a latch retainer disposed on the stationary handle, wherein the latch and latch retainer are configured to releasably maintain the lever in its second position. The latch retainer can be biased proximally.

In preferred embodiments, a predetermined amount of movement of the first jaw member from the approximated position towards its spaced position causes distal movement of the latch retainer to release the latch.

In some embodiments, the safety mechanism includes a plate disposed in mechanical cooperation with the stationary handle, and the plate is biased distally. A lip of the plate preferably prevents movement of the lever towards its second position.

The lever is preferably configured to mechanically engage the firing trigger when the lever is in its first position, the firing trigger fires a plurality of fasteners from the first jaw into contact with the second jaw.

The present disclosure provides in another aspect a surgical instrument comprising a handle assembly including a stationary handle, an approximation mechanism, and a firing trigger for firing a plurality of fasteners. A safety mechanism is disposed in mechanical cooperation with the handle assembly and is movable between a first position to prevent firing of the fasteners and a second position to enable firing of the fasteners. The safety mechanism is retained in the second position. An elongated body portion extends distally from the handle assembly. A head portion is disposed adjacent a distal end of the elongated body portion and includes a first jaw member and a second jaw member, the first jaw member being movable in relation to the second jaw member between spaced and approximated positions. An approximation mechanism moves the first jaw member in relation to the second jaw member from a spaced position to an approximated position, wherein movement of the first jaw member in relation to the second jaw member from the approximated position towards the spaced position prior to firing of the fasteners causes the safety mechanism to be released to move from its second position to its first position.

In some embodiments, the plurality of fasteners are retained in the second jaw.

In preferred embodiments, the safety mechanism includes a lever retained by a latch retainer in the second position. Preferably, a predetermined amount of movement of the first jaw member from the approximated position towards the spaced position causes distal movement of the latch retainer to release the latch.

In some embodiments, the safety mechanism includes a plate disposed in mechanical cooperation with the stationary handle, the plate being biased distally and moved by the movement of the approximation mechanism. The lip of the plate in some embodiments prevents movement of the lever towards its second position.

DESCRIPTION OF THE DRAWINGS

Various embodiments of the presently disclosed surgical stapling instrument are disclosed herein with reference to the drawings, wherein.

DETAILED DESCRIPTION

Figure 1:
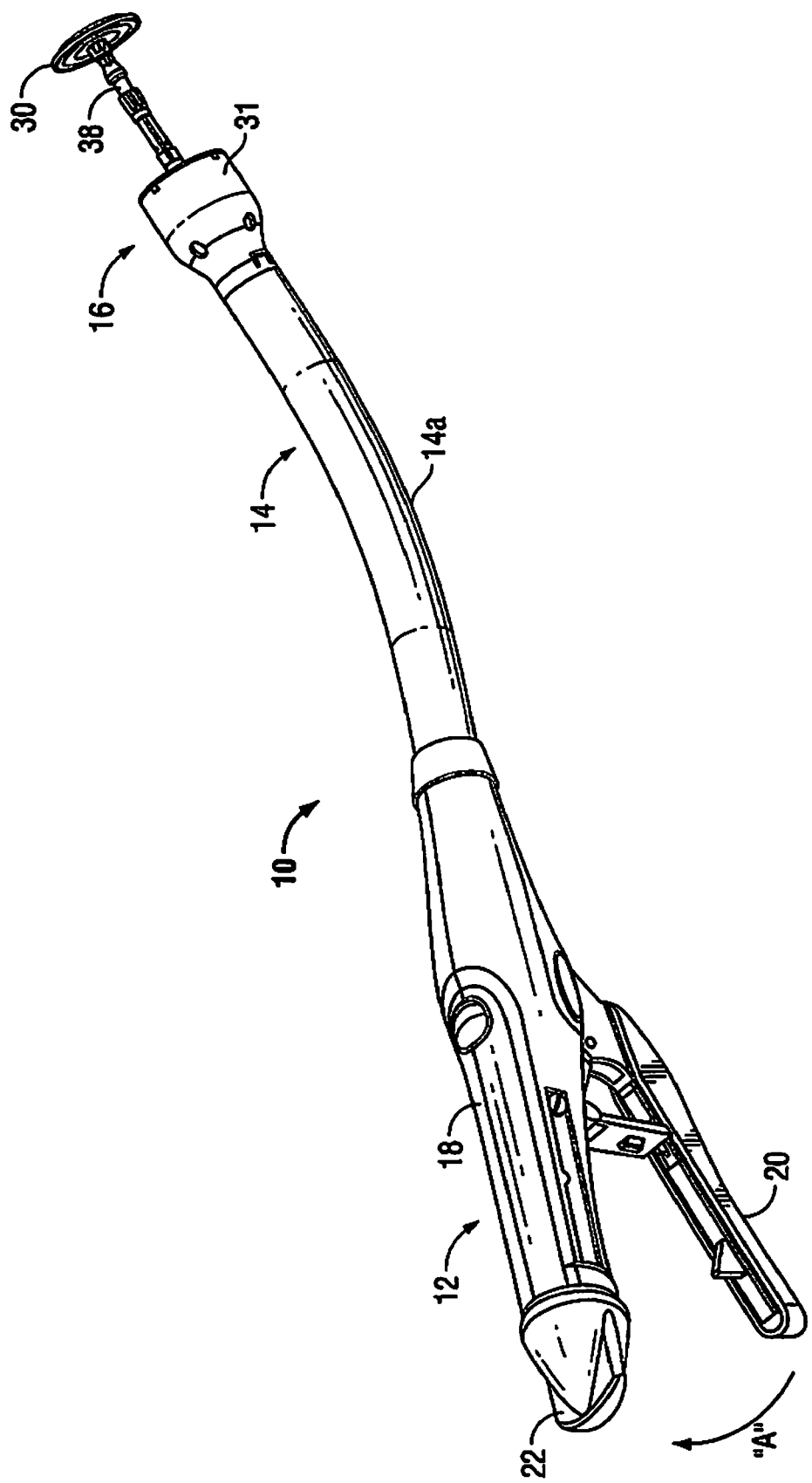
FIG. 1 is a perspective view of the presently disclosed surgical stapling instrument illustrated in an unapproximated position, in accordance with an embodiment of the present disclosure.

Embodiments of the presently disclosed surgical stapling instrument will now be described in detail with reference to the drawings in which like reference numerals designate identical or corresponding elements in each of the several views.

Throughout this description, the term "proximal" will refer to the portion of the instrument closer to the operator and the term "distal" will refer to the portion of the instrument farther from the operator.

Figure 2:
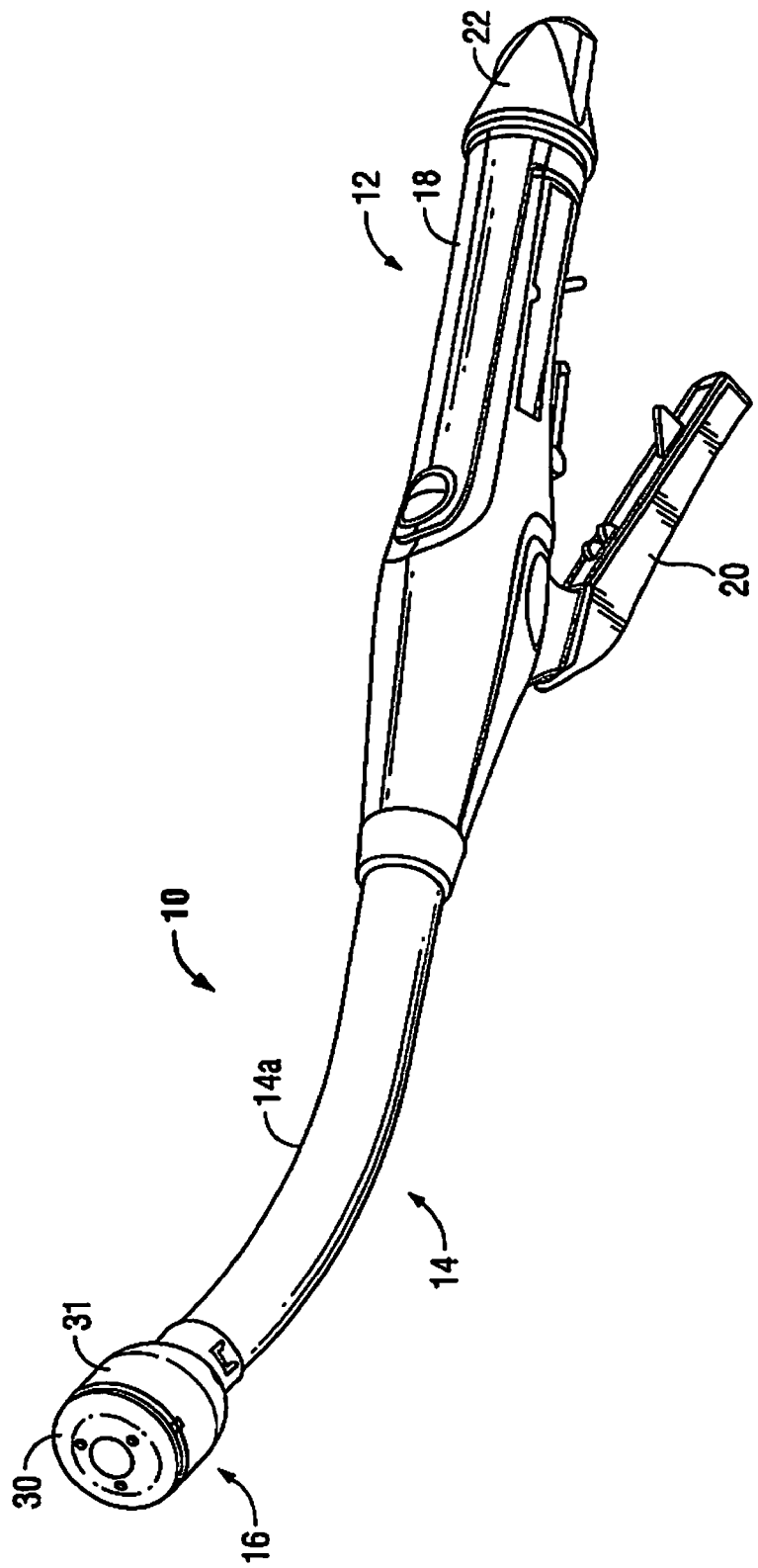
FIG. 2 is a perspective view of the surgical stapling instrument of FIG. 1 illustrated in an approximated position.
Figure 3:
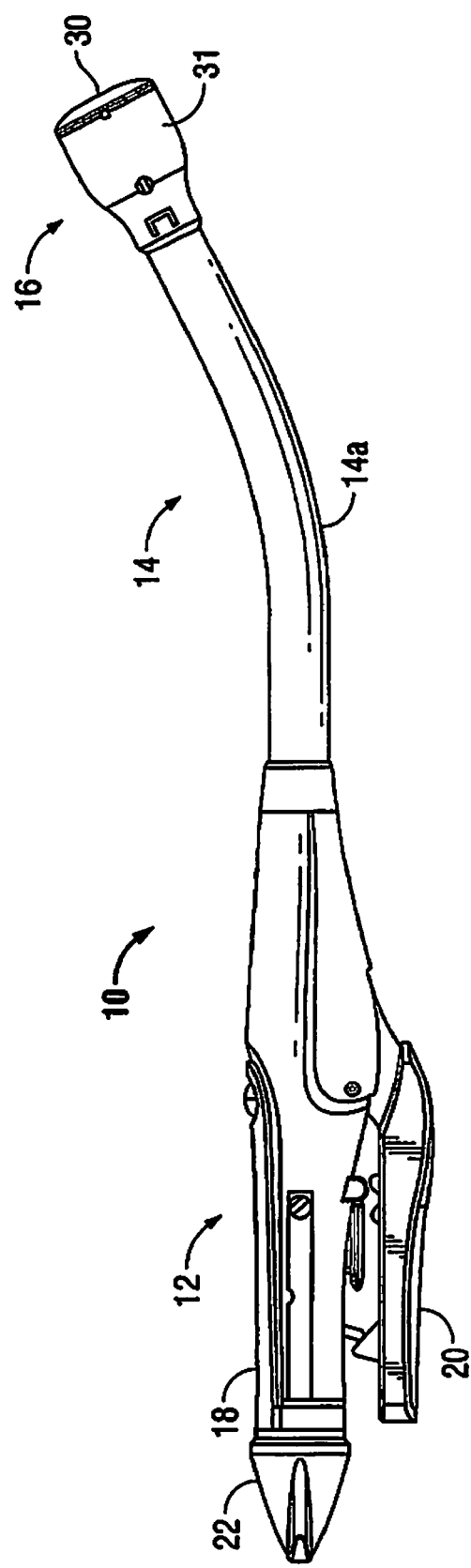
FIG. 3 is a side view of the surgical stapling instrument of FIGS. 1 and 2 illustrated in a fired position.

FIGS. 1-3 illustrate one embodiment of the presently disclosed surgical stapling instrument and is generally referred to as reference number 10. Briefly, surgical stapling instrument 10 includes a handle assembly 12, an elongated body portion 14 including a curved elongated outer tube 14a, and a head portion 16. Alternately, in some surgical procedures, e.g., the treatment of hemorrhoids, it is desirable to have a substantially straight body portion. It is contemplated herein that the length, shape and/or the diameter of body portion 14 and head portion 16 may also be varied to suit a particular surgical procedure.

With continued reference to FIGS. 1-3, handle assembly 12 includes a stationary handle 18, a firing trigger 20, and a rotatable approximation mechanism 22. Head portion 16 includes a first jaw member (e.g., an anvil assembly 30) and a second jaw member (e.g., a shell assembly 31). Anvil assembly 30 is movable in relation to shell assembly 31 between spaced and approximated positions.

With continued reference to FIGS. 1-3, in operation, rotation of approximation mechanism 22 causes movement of anvil assembly 30 in relation to shell assembly 31 between spaced (FIG. 1) and approximated (FIGS. 2 and 3) positions, as approximation mechanism 22 is mechanically engaged with anvil retainer 38 (FIG. 1), which is fastened to anvil assembly 30. It is envisioned that rotation of approximation mechanism 22 in a first direction (e.g., clockwise) causes proximal movement of anvil assembly 30 (i.e., towards its approximated position), and rotation of approximation mechanism 22 in a second opposite direction (e.g., counterclockwise) causes distal movement of anvil assembly 30 (i.e., towards its spaced position). Details of the approximation are disclosed for example in U.S. Pat. No. 7,303,106, the entire contents of which are incorporated herein by reference.

Actuation of firing trigger 20 (i.e., pivoting in the direction of arrow "A" in FIG. 1), causes staples to be ejected from shell assembly 31 towards anvil assembly 30. That is, firing trigger 20 is disposed in mechanical cooperation with a pusher (not explicitly shown in the illustrated embodiments), such that actuation of firing trigger 20 causes advancement of the pusher into contact with the staples, which ejects the staples into staple deforming pockets of anvil assembly 30. Details of the firing are disclosed for example in U.S. Pat. No. 7,303, 106, the entire contents of which are incorporated herein by reference.

Referring now to FIGS. 4-9, approximation mechanism 22 is mechanically engaged with a screw stop 40 and screw stop 40 is in mechanical cooperation with anvil assembly 30 (not shown). Here, rotation of approximation mechanism 22 in a first direction causes screw stop 40 to move proximally, which in turn causes proximal movement of anvil assembly 30. As screw stop 40 moves proximally, a portion 42 thereof (see FIG. 9A) urges a portion (i.e., a plate 250) of safety mechanism 200 proximally against the bias of a plate spring 260, as discussed in more detail below. As a result, a lever 210 pivots in the direction of arrow "C" in FIG. 6 to permit firing of surgical stapling instrument 10. That is, when lever 210 is in its first, blocking position (FIGS. 4-6), actuation of firing trigger 20 is prevented.

More particularly, and with continued reference to FIGS. 4-9, safety mechanism 200 (which is broken down into a first portion 200a (FIGS. 4 and 7) and a second portion 200b (FIGS. 5 and 8), discussed in further detail below, is disposed in mechanical cooperation with handle assembly 12 and maintains firing trigger 20 in an open position (FIGS. 4-6) until anvil assembly 30 and shell assembly 31 have been approximated. Safety mechanism 200 is also configured to prevent the actuation of firing trigger 20 when anvil assembly 30 is moved relative to shell assembly 31 from their approximated position towards their spaced position. That is, if the anvil assembly 30 and shell assembly 31 are in their approximated position (e.g., clamping tissue) and are then moved towards their spaced position (e.g., unclamping tissue), safety mechanism 200 prevents actuation of firing trigger 20 until anvil assembly 30 and shell assembly 31 return to their approximated position. Thus, as can be appreciated, safety mechanism 200 helps prevent staples from being fired prematurely.

Figure 4:
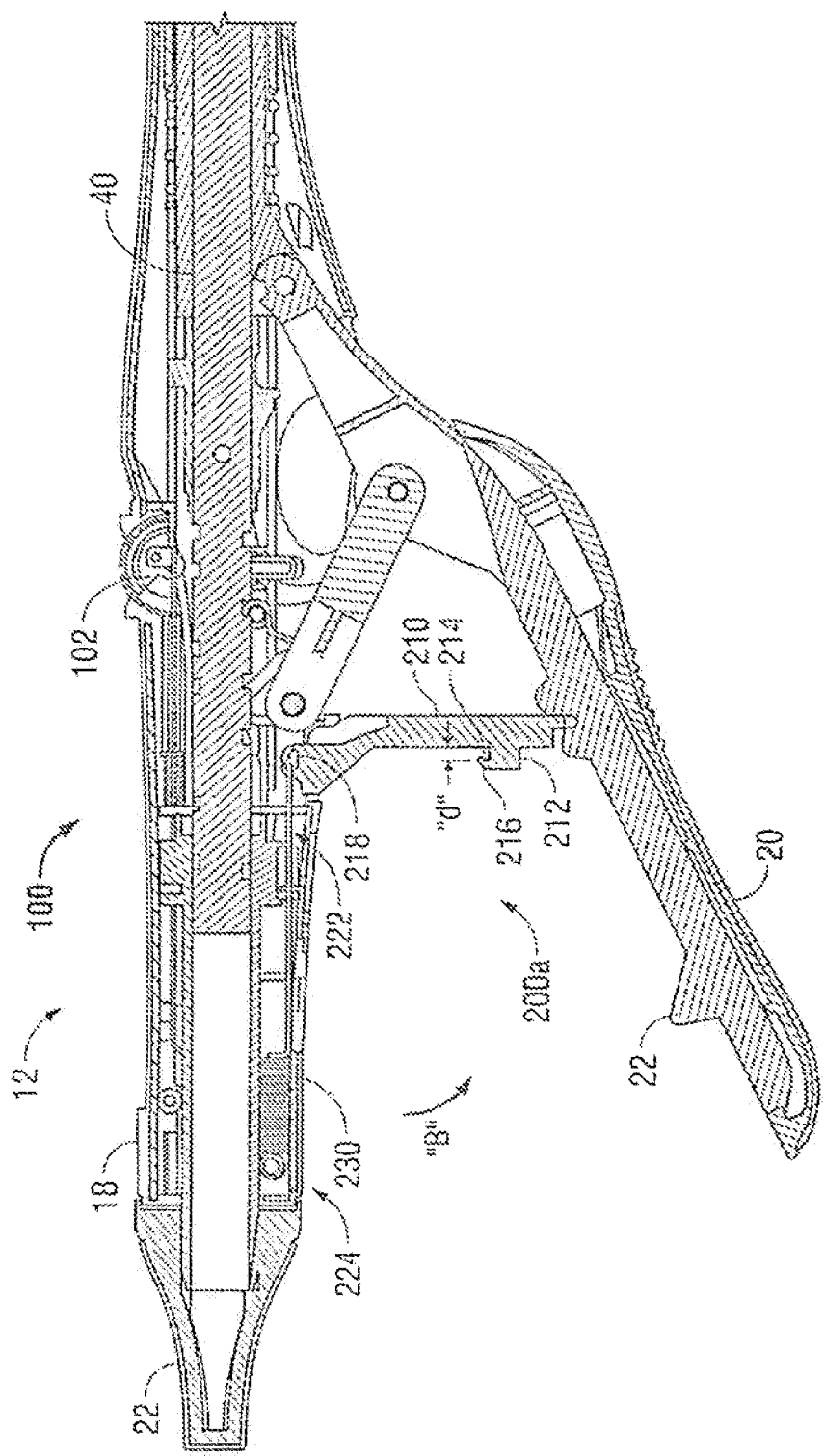
FIG. 4 is an longitudinal, cross-sectional view of a portion of the surgical stapling instrument in the unapproximated position and a first portion of a safety mechanism in a first position.
Figure 5:
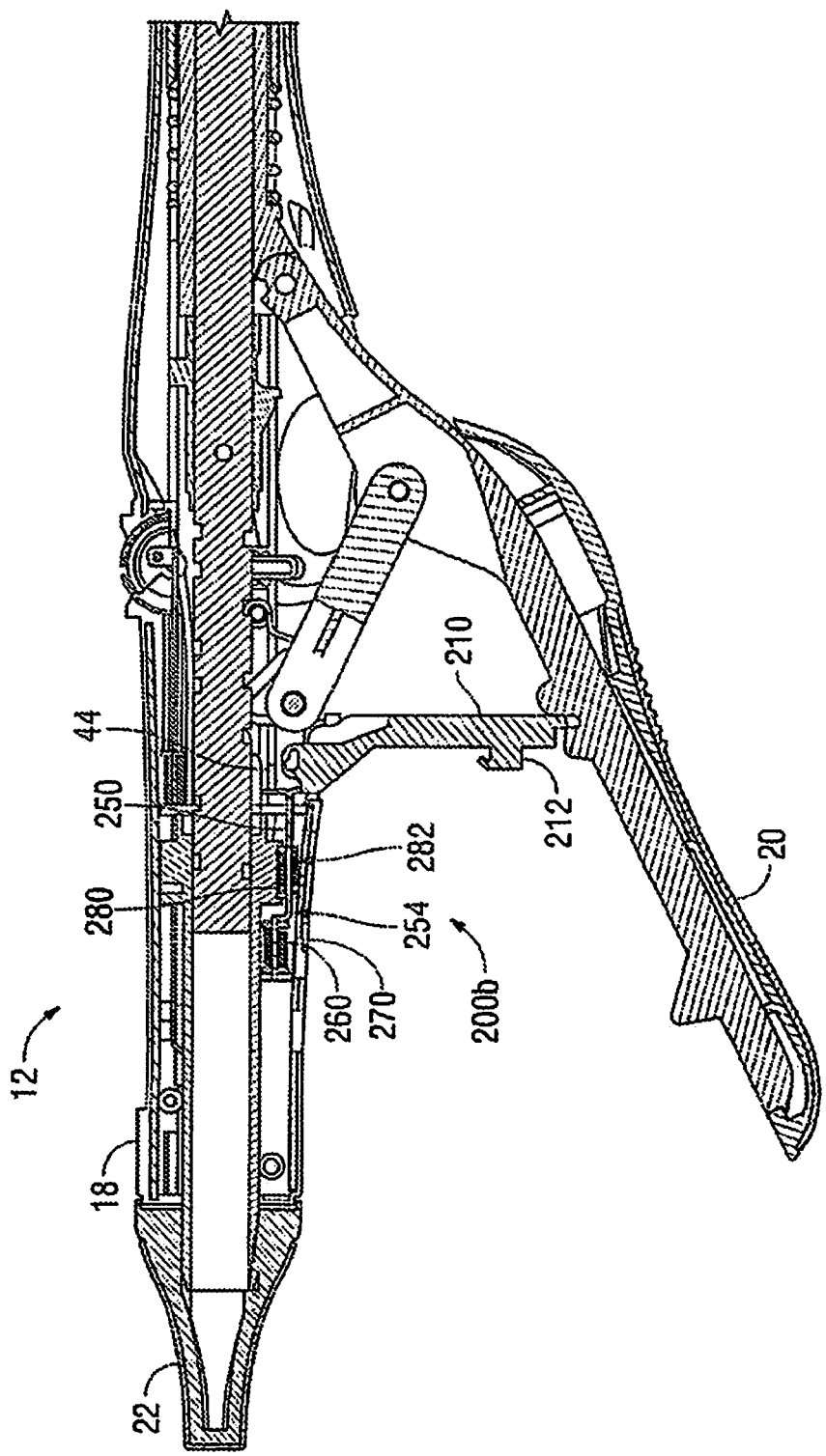
FIG. 5 is an longitudinal, cross-sectional view of a portion of the surgical stapling instrument in the unapproximated position and a second portion of the safety mechanism in a first position.
Figure 6:
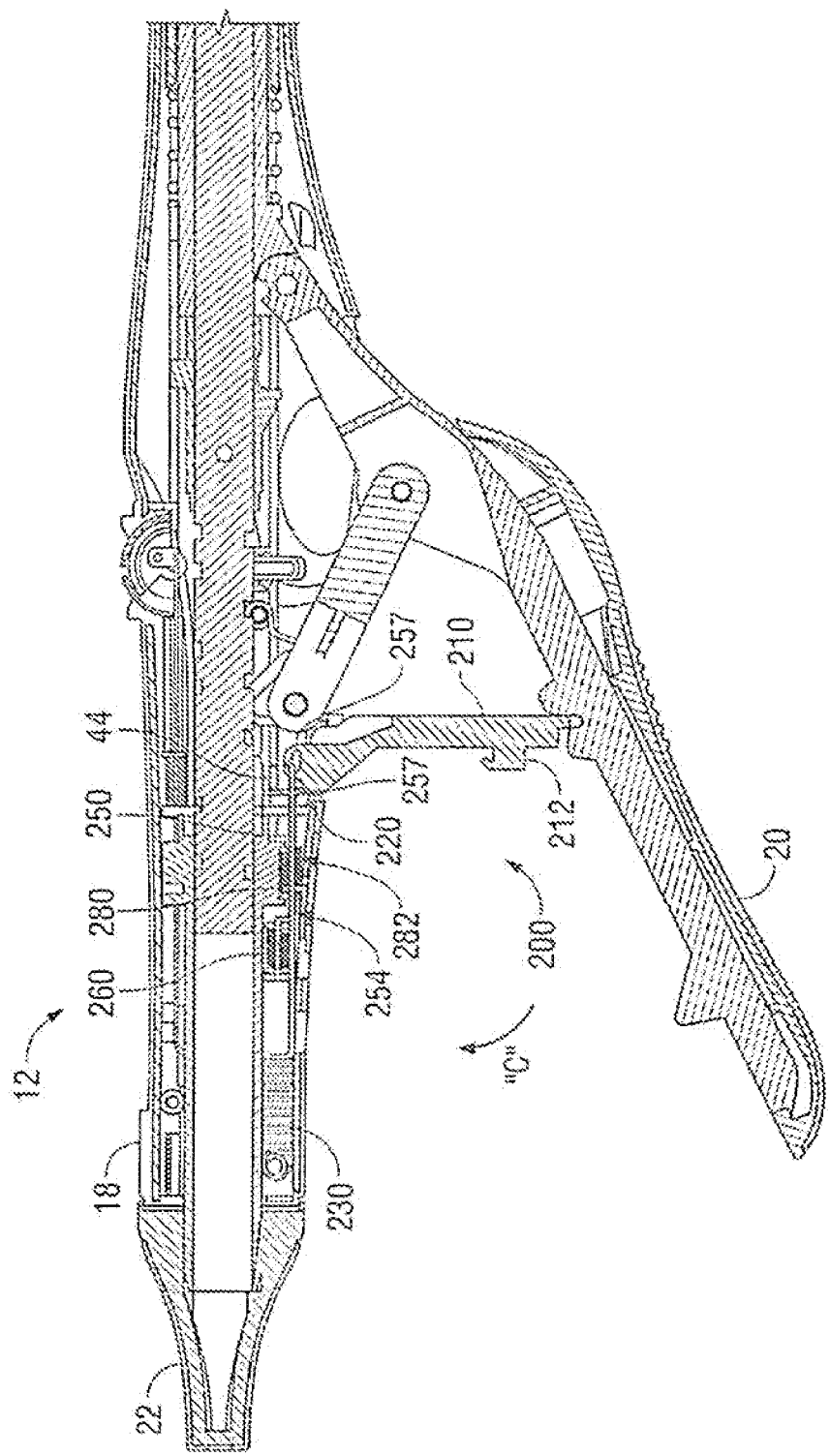
FIG. 6 is an longitudinal, cross-sectional view of a portion of the surgical stapling instrument in the unapproximated position and the first portion and the second portion of the safety mechanism in the first position.
Figure 7:
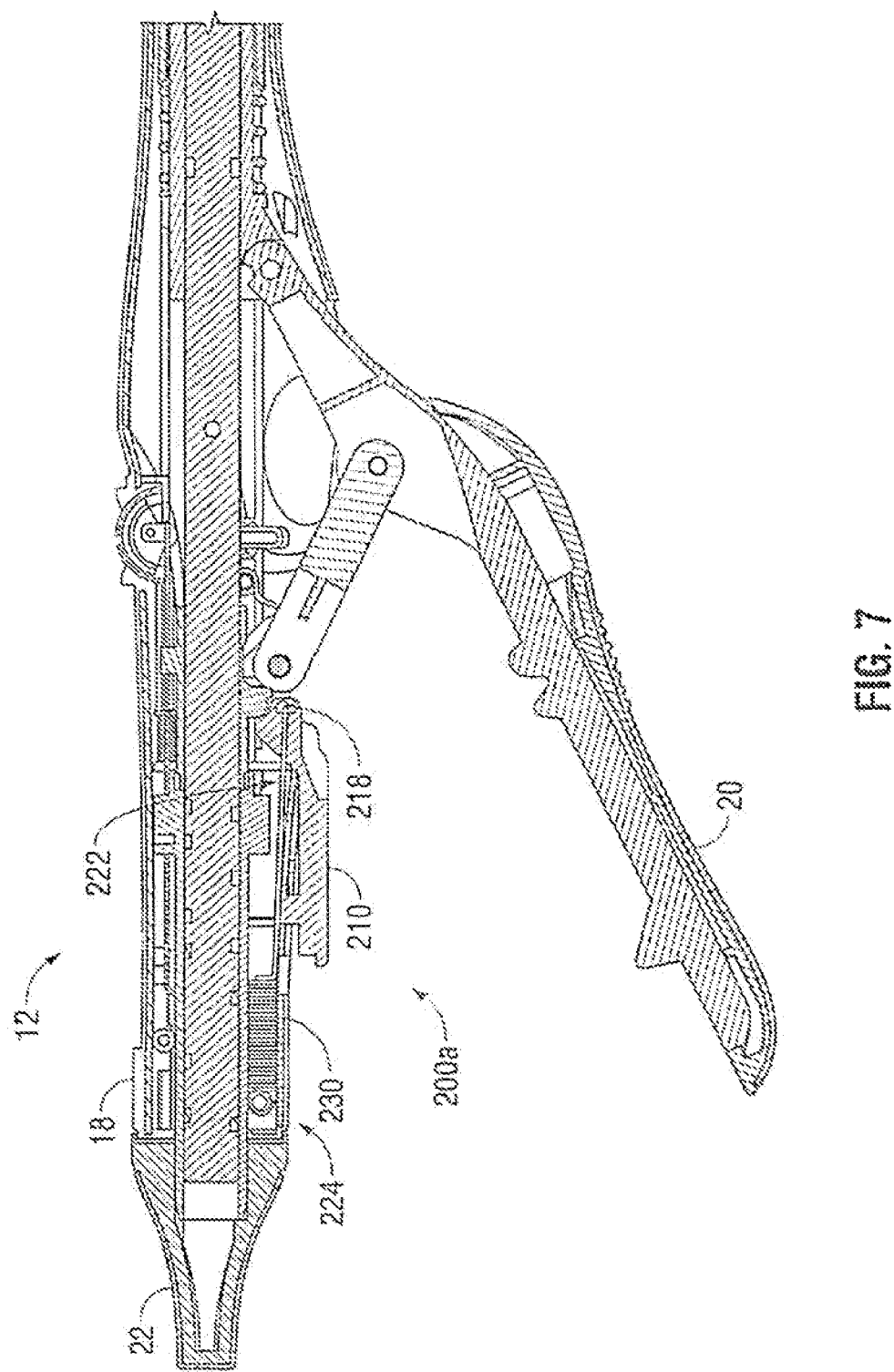
FIG. 7 is a longitudinal, cross-sectional view of a portion of the surgical stapling instrument in the approximated position and the first portion of the safety mechanism in a second position.
Figure 8:
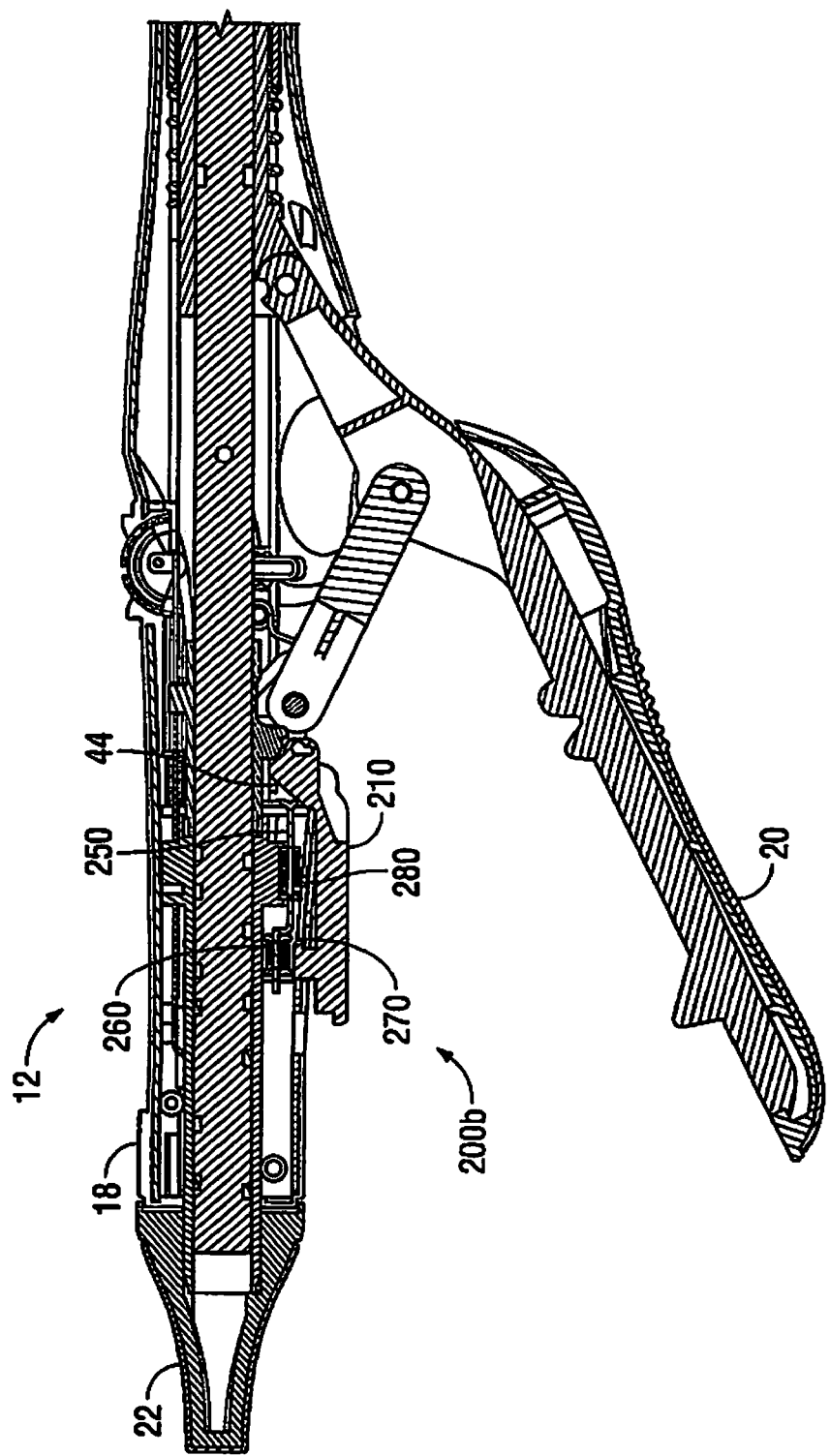
FIG. 8 is a longitudinal, cross-sectional view of a portion of the surgical stapling instrument in the approximated position and the second portion of the safety mechanism in a second position.
Figure 9:
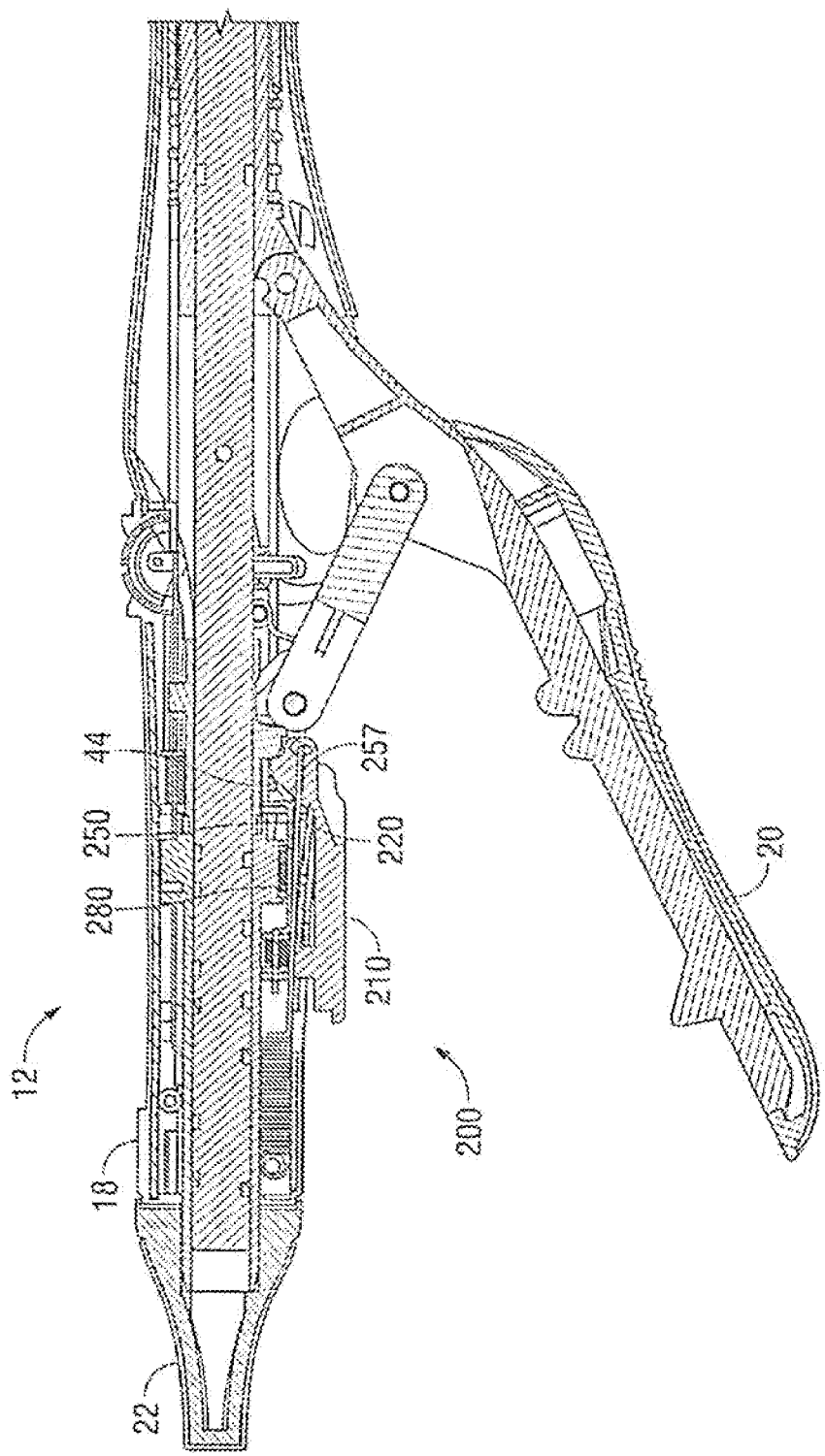
FIG. 9 is a longitudinal, cross-sectional view of a portion of the surgical stapling instrument in the approximated position and the first portion and the second portion of the safety mechanism in the second position.

Various components of safety mechanism 200 are shown in FIGS. 4-9, with several components omitted in some figures for clarity. FIGS. 4-6 illustrate safety mechanism 200 in its first, locking position. FIGS. 7-9 illustrate safety mechanism 200 in its second, unlocked position. For ease of viewing clarity, as noted above, safety mechanism 200 has been broken down into a first portion 200a (shown individually in FIGS. 4 and 7) and a second portion 200b (shown individually in FIGS. 5 and 8). Both first portion 200a and second portion 200b of safety mechanism 200 are shown in FIGS. 6 and 9.

With initial reference to FIGS. 4 and 7, first portion 200a of safety mechanism 200 includes lever 210 having a latch 212, and a safety spring 230. Lever 210 is pivotably disposed with respect to stationary handle 18. Latch 212, which is shown integrally formed with lever 210, includes a tooth 214 having an angled surface 216 thereon. A distance "d" is defined between tooth 214 and a surface 216 of lever 210 (see FIG. 4).

A distal portion 222 of safety spring 230 is configured to mechanically engage (e.g., pivotably engage) an aperture 218 of lever 210. A proximal portion 224 of safety spring 230 engages (e.g., is pinned to) a portion of stationary handle 18. Safety spring 230 is configured to bias lever 210 in the substantial direction of arrow "B" in FIG. 4.

Second portion 200b of safety mechanism 200 is illustrated in FIGS. 5 and 8. Second portion 200b includes plate 250 (an enlarged view of which is shown in FIG. 10), plate spring 260, a latch retainer 270, and a retainer spring 280. Plate 250 is disposed within stationary handle 18 and, as discussed above, plate 250 is configured for engagement by a portion of screw stop 40. More specifically, as screw stop 40 moves proximally, screw stop 40 contacts a distal portion 252 of plate 250 (see FIGS. 9A and 10), thus creating a proximal force against plate 250. Plate spring 260, which is also disposed within stationary handle 18, is in mechanical cooperation with a proximal portion 254 of plate 250 and is configured to distally bias plate 250 against the proximal force exerted thereon by screw stop 40. A rib 44 is disposed within stationary handle 18 and is configured and positioned to limit the distal translation of plate 250 (see FIGS. 5, 8 and 9A). More specifically, at least one of tabs 253 (see FIG. 10) of plate 250 is configured to engage rib 44.

With continued reference to second portion 200b of safety mechanism 200 in FIGS. 5 and 8, latch retainer 270 and retainer spring 280 are illustrated. Latch retainer 270 is disposed in mechanical cooperation with plate 250 and is slidably engaged therewith. Latch retainer has several detents to engage the wall adjacent opening 258 in plate 250. Retainer spring 280 is disposed with stationary handle 18 and is configured to bias latch retainer 270 proximally with respect to plate 250. It is envisioned that a distal portion 282 of retainer spring 280 mechanically engages a portion 256 of plate 250 (see FIG. 10). As discussed in detail below, the interaction between latch retainer 270, retainer spring 280 and plate 250 is configured to allow releasable engagement between latch 212 and latch retainer 270. A proximal portion 284 of retainer spring 280 mechanically engages a portion of latch retainer 270.

In use, and with reference to FIGS. 6, 9 and 10, a distal lip 257 of plate 250 contacts a blocking surface 220 of lever 210 (FIG. 5), thus preventing rotation (i.e., in the substantial direction of arrow "C" in FIG. 6 of lever 210 until plate 250 is proximally moved a sufficient distance such that distal lip 257 proximally passes blocking surface 220 of lever 210. It is envisioned that rotation of approximation knob 22 such that anvil assembly 30 and shell assembly. 31 are approximated causes screw stop 40 to proximally translate a sufficient distance so tab portion 42 causes distal lip 257 to proximally pass blocking surface 220 (against the bias of plate spring 260). That is, once anvil assembly 30 and shell assembly 31 are approximated (e.g., clamping tissue therebetween), lever 210 is free to rotate (e.g., manually) from its first blocking position (FIGS. 4-6) to its second enabling position (FIGS. 7-9) in the substantial direction of arrow "C" (against the bias of safety spring 230), thus enabling actuation of firing trigger 20.

Figure 9A:
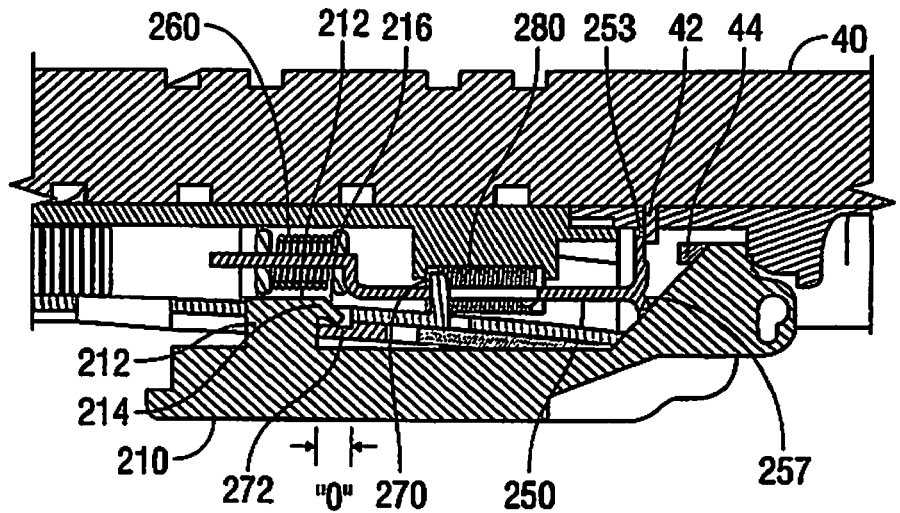
FIG. 9A is an enlarged view of a portion of the surgical stapling instrument of FIG. 9.
Figure 10:
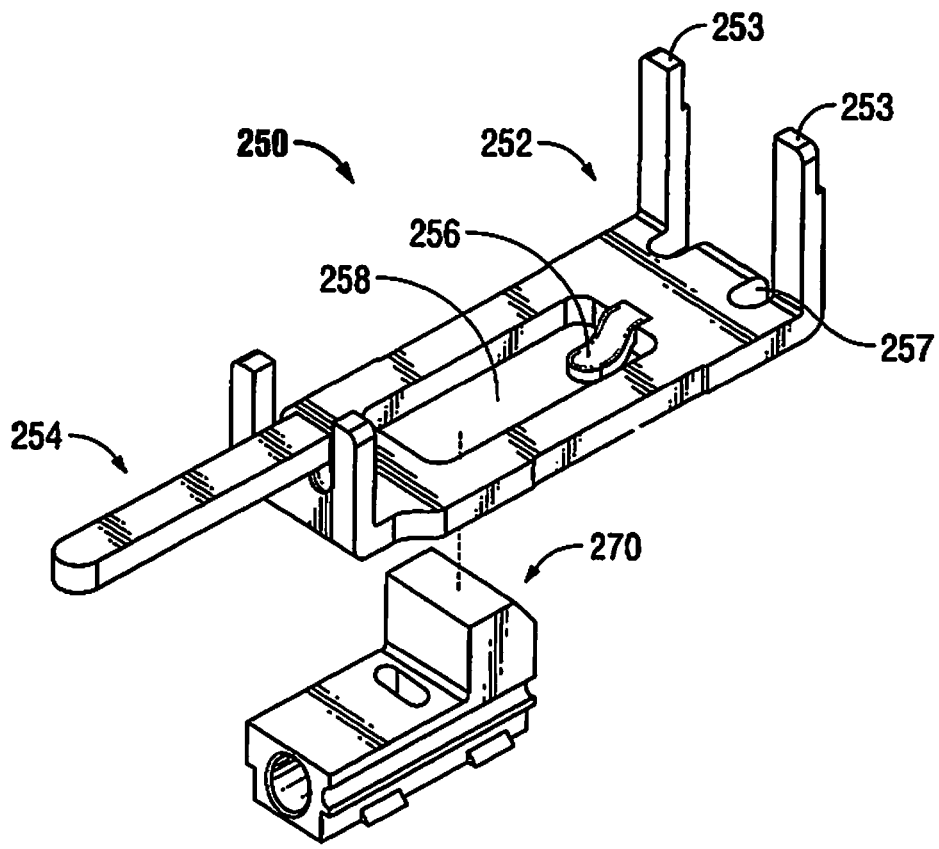
FIG. 10 is a perspective view of a safety plate and latch retainer of the second portion of the safety mechanism as illustrated in FIGS. 5, 6, 8, 9 and 9A.

With regard to FIG. 9A, an enlarged view of the interaction between latch 212 and latch retainer 270 is shown. When lever 210 is rotated from its first blocking position to its second enabling position, latch 212 engages latch retainer 270. More particularly, angled surface 216 of latch 212 is configured to make initial contact with latch retainer 270. The force exerted by rotation of lever 210 causes angled surface 216 of latch 212 to distally translate latch retainer 270, with respect to plate 250, against the bias of retainer spring 280. After latch retainer 270 is distally translated and tooth 214 of latch 212 passes a securing member 272 of latch retainer 270, latch retainer 270 is translated proximally via the bias of retainer spring 280, such that securing member 272 is urged into the distance "d" between tooth 214 and surface 216 of lever 210. In this position, latch 212 is releasably retained by latch retainer 270, and actuation of firing trigger 20 is enabled.

If anvil assembly 30 and shell assembly 31 are moved towards their spaced position (e.g., via rotation of approximation knob 22 in the second direction), thus possibly unclamping tissue, safety mechanism 200 is configured such that lever 210 moves to its first, blocking position, thus preventing the firing of staples. In particular, as anvil assembly 30 and shell assembly 31 are moved towards their spaced position, screw stop 40 is moved distally. Thus, the portion 42 of screw stop 40 that had been in contact with and proximally urging distal portion 252 of plate 250, also moves distally. Consequently, the distal bias of plate spring 260 is not sufficiently resisted and plate 250 is distally translated. Upon distal translation of plate 250, latch retainer 270 and retainer spring 280 also translate distally (to a release point, as discussed below) such that latch retainer 270 releases latch 212. The release of latch 212, in combination with the bias asserted by safety spring 230, causes lever 210 to move towards its first, blocking position. Therefore, safety mechanism 200 prevents actuation of firing trigger 30 after unclamping of tissue (i.e., anvil assembly 30 and shell assembly 31 are moved towards their spaced (unapproximated) position.

As can be appreciated, the tolerances of various components of safety mechanism 200 help determine the amount of unclamping that is sufficient to return lever 210 to its first, blocking position. For example, the release point may be dependent on an overlap "O" (FIG. 9A) between latch 212 and securing member 272 of latch retainer 270. It is envisioned that the overlap "O" may be between about 0.010 inches and about 0.080 inches, for example, depending on the desired effect. Other distances are also contemplated. In such an example, the smaller the overlap "O," the lower amount of unclamping that will be necessary to cause lever 210 to return to its first, blocking position, and vice versa.

The present disclosure also contemplates the use of an indicator mechanism 100, as shown in FIGS. 4-9. In the first position, indicator 102 provides indication to a surgeon that the instrument is in an open, non-approximated position. In the second position, indicator 102 provides indication to a surgeon that the instrument has been approximated and is now in a fire-ready position. In the third position, indicator 102 provides indication to a surgeon that the instrument has been fired. Further details of indicator mechanism are shown and described in U.S. Pat. No. 7,303,106, incorporated hereinabove by reference.

The present disclosure also relates to a method of performing a surgical procedure. The method comprises the step of providing a surgical instrument, as described above, positioning the surgical instrument adjacent a surgical site, and moving anvil assembly 30 with respect to shell assembly 31 from its approximated position towards its spaced position to move the portion (e.g., lever 210) of safety mechanism 200 from its second position to its first position.

Further details of other features of surgical instrument 10, such as the approximation assembly, firing assembly, and lock out mechanism are disclosed in commonly-owned U.S. Pat. Nos. 7,168,604 and 7,303,106, the entire contents of each of which are incorporated by reference herein.

It will be understood that various modifications may be made to the embodiments disclosed herein. For example, the disclosed safety mechanism may be used with other types of surgical instruments for joining tissue, such as, for example, surgical stapling instrument with linear jaw members, surgical instruments with curved jaw members and vessel sealing instruments. Further details of a linear surgical stapling instrument are described in detail in commonly-owned U.S. Pat. No. 6,953,139 to Milliman et al., the entire contents of which are hereby incorporated by reference herein. An example of a commonly-owned vessel sealing instrument is disclosed in U.S. Pat. No. 7,118,570, the entire contents of which are hereby incorporated by reference herein. Therefore, the above description should not be construed as limiting, but merely as exemplifications of disclosed embodiments. Those skilled in the art will envision other modifications within the scope and spirit of the claims appended hereto.

What is claimed is:

1. A surgical instrument, comprising:
   a handle assembly including an approximation mechanism and a firing mechanism;
   an elongated body portion extending distally from the handle assembly;
   a head portion disposed adjacent a distal end of the elongated body portion and including an anvil assembly and shell assembly supporting a plurality of staples, the approximation mechanism being actuable to move the head portion between spaced and approximated positions and the firing mechanism being actuable to eject the plurality of staples from the shell assembly; and
   a safety mechanism disposed in mechanical cooperation with the handle assembly, the safety mechanism being movable from a first position preventing actuation of the firing mechanism to a second position permitting actuation of the firing mechanism, wherein the safety mechanism is adapted to move automatically from the second position to the first position in response to movement of the head portion from the approximated position towards the spaced position.

2. The surgical instrument of claim 1, wherein the safety mechanism includes a lever which is movable from the first position to prevent actuation of the firing mechanism to the second position to permit actuation of the firing mechanism.

3. The surgical instrument of claim 2, wherein handle assembly includes a firing trigger, the lever being pivotal from the first position in engagement with the firing trigger to the second position out of engagement with the firing trigger.

4. The surgical instrument of claim 3, wherein the safety mechanism includes a slidable member which is movable from a distal position preventing movement of the lever from the first position to the second position to a proximal position permitting movement of the lever from the first position to the second position.

5. The surgical instrument of claim 4, wherein approximation mechanism includes a screw stop, the screw stop being movable into engagement with the slidable member as the head portion is moved from the spaced position to the approximated position to move the slidable member from the distal position to the proximal position.

6. The surgical instrument of claim 5, further including a biasing member positioned to urge the slidable member towards the distal position.

7. The surgical instrument of claim 6, wherein the lever is manually movable from the first position to the second position to enable actuation of the firing mechanism when the head portion is in the approximated position.

8. The surgical instrument of claim 6, wherein the safety mechanism includes a latch and a latch retainer, the latch and latch retainer being configured to releasably maintain the lever in the second position when the head portion is in the approximated position.

9. The surgical instrument of claim 8, wherein the latch is supported on the lever and is positioned to engage the latch retainer when the lever is in the second position.

10. The surgical instrument of claim 8, further including a latch retainer biasing member positioned to urge the latch retainer proximally.

11. The surgical instrument of claim 10, wherein the latch retainer is supported on the slidable member such that actuation of the approximation mechanism to move the head portion from the approximated position towards the spaced position allows the slidable member biasing member to effect distal movement of the slidable member and the retainer to disengage the latch retainer from the latch.

12. The surgical instrument of claim 11, wherein the lever biasing member is positioned to move the lever from the second position to the first position upon movement of the latch retainer distally a predetermined amount.

13. The surgical instrument of claim 1, wherein the firing mechanism is actuable to fire a plurality of fasteners from the shell assembly into contact with the anvil assembly.

* * * * *